United States Patent [19]
Ward et al.

[11] Patent Number: 5,486,536
[45] Date of Patent: Jan. 23, 1996

[54] SULFATIDES AS ANTI-INFLAMMATORY COMPOUNDS

[75] Inventors: Peter A. Ward, Ann Arbor, Mich.; Masayuka Miyasaka, Suita; Yasuo Suzuki, Shizuoka, both of Japan

[73] Assignee: The Regents of the University of Michigan, Ann Arbor, Mich.

[21] Appl. No.: 289,585

[22] Filed: Aug. 15, 1994

[51] Int. Cl.$^6$ .................................................. A61K 31/35
[52] U.S. Cl. .................................................. 514/460
[58] Field of Search ............................................ 514/460

[56] References Cited

PUBLICATIONS

Mulligan et al, "Neutrophil–dependent Acute Lung Injury", J. Clin. Invest., vol. 90, Oct. 1992, pp. 1600–1607.

Mulligan et al, "Protective Effects of IL–4 and IL–10 Against Immune Complex–Induced Lung Injury", The Journal of Immunology, vol. 151, No. 10, Nov. 1993, pp. 5666–5674.

Handa et al, "Inhibition Of Infection With Human Immunodeficiency Virus Type 1 By Sulfated Gangliosides", Biochemical and Biophysical Research Communications, vol. 175, No. 1, Feb. 1991, pp. 1–9.

Bajorath, et al. *Biochemistry* (Feb. 1994), 33(6), 1332–9.

*Primary Examiner*—José G. Dees
*Assistant Examiner*—Joseph M. Conrad, III
*Attorney, Agent, or Firm*—Oblon, Spivak, McClelland, Maier & Neustadt

[57] ABSTRACT

Using in vitro adhesion of recombinant rat L-selectin-Ig or rat neutrophils, it has been demonstrated that these materials bind to sulfatide that has been present in solid phase on a plastic surface. The binding activity appears to have structural requirements, with the sulfate group being critically present in position 3 on the pyranose ring of galactose. When used in vivo, it has been demonstrated that sulfated glycolipids such as brain sulfatide and ganglioside, have significantly protective effects in two models of lung inflammation, the first systemic activation of complement and the second occurring after intrapulmonary deposition of immune complexes. Both inflammatory reactions are complement, neutrophil and selectin-dependent. The protective effects of these compounds are linked to their ability to prevent the recruitment of neutrophils into lung tissue. On the basis of these findings, it is demonstrated by sulfatides and related compounds have significant in vivo anti-inflammatory activities. These compounds thus represent a new class of anti-inflammatory agents.

12 Claims, No Drawings

SULFATIDES AS ANTI-INFLAMMATORY COMPOUNDS

This invention was made with government support under Grant Number AI-33189 awarded by the National Institute of Health. The government has certain rights in this invention.

BACKGROUND OF THE INVENTION

1. Field of the Invention

The present invention provides methods of treatment and prevention of selectin-dependent acute lung injury and diseases which result from selectin-dependent acute lung injury by administration of a sulfatide. The present invention also provides pharmaceutical compositions for the treatment and prevention of inflammatory lung injury and diseases which selectin-dependent.

2. Discussion of the Background

Acute lung injury develops following systemic activation and intrapulmonary deposition of IgG immune complexes in rats. Previously, acute lung injury has been treated in in vivo models with the use of antibodies (M. S. Mulligan et al, *J. Immunol.*, In press (1994); M. S. Mulligan et al., *J. Clin. Invest.* 90, 1600 (1992)), selectin-Ig chimeras (M. S. Mulligan et al., *J. Immunol.* 151, 1 (1993)), synthetic fucosylated sialylated oligosaccharides (M. S. Mulligan et al., *Nature* 364, 149 (1993); M. S. Mulligan, et al., *J. Exp. Med.*, 178, 623 (1993)) and a mixture of IL-4 and IL-10 (M. S. Mulligan et al., *J. Immunol.* 151, 5666 (1993)).

Selectins (L-, E- and P-) are lectin binding molecules that facilitate adhesive interactions between endothelial cells and leukocytes. This adhesion-promoting process causes the "rolling" phenomenon of leukocytes along endothelial surfaces and represents the first step in events that ultimately lead to leukocyte transmigration (reviewed, J. C. Paulson, in *Adhesion: Its Role in Inflammatory Disease*, J. M. Harlan, and D. Y. Lui, Eds. (W. H. Freeman and Co., New York, 1991). Current approaches for the in vivo blocking of selectin-dependent inflammatory reactions featuring the recruitment of neutrophils rely on the use of blocking antibodies to selectins (M. A. Jutila et al, *J. Immunol.*, 143, 3318 (1989); M. S. Mulligan et al, *J. Immunol.*, 152, 832 (1994)), sialyl Lewis$^x$ (a fucosylated and sialylated oligosaccharide known to bind to selectins) (M. S. Mulligan et al., *Nature* 364, 149 (1993); M. S. Mulligan, et al., *J. Exp. Med.*, 178, 623 (1993)), or the use of selectin-Ig chimeric proteins (S. R. Watson et al., *Nature* 349, 164 (1991); M. S. Mulligan et al., *J. Immunol.* 151, 1 (1993)).

Besides the family of oligosaccharides that are reactive with lectin binding sites on selectins, additional ligands are also known. These include sulfated glycolipids (such as sulfatides and seminolipids) (Y. Suzuki, et al., *Biochem. Biophys. Res. Comm.* 190, 426 (1993)), a sulfated and sialylated mucin-like molecule which is present in high venular endothelial cells of lymph nodes and has been termed Gly-CAM-1 (L. A. Laskey et al., *Science* 361, 555 (1993); L. A. Laskey et al., *Cell* 69, 927 (1991)), a sulfated heparin-like molecule extracted from endothelial cells (K. E. Nogard-Sumnicht, et al., *Science* 261, 480 (1993)), sulfated glycans (fucoidin, dextran sulfate) (L. M. Stoolman, et al., *Cell. Biol.* 99, 1535 (1984); T. A. Yednock, et al., *J. Cell. Biol.* 104, 713 (1987)), a sulfoglucuronyl glucosphingolipid (Needham and Schnaar, *Proc. Nat'l. Acad. Sci. USA,* 90, 1355 (1993)), CD34 sialomucin (S. Baumhueter et al., *Science* 262, 436 (1993)), and sulfated oligosaccharides (such as sialyl Lewis$^x$ and sialyl Lewis$^a$) (C-T. Yuen et al., *Biochem.* 31 9126 (1992)). Most of these lectins are reactive with L-selectin, while binding to P- and E-selectin has been variously reported (G. Todderud et al., *J. Leukoc. Biol.* 52, 85 (1992)). Virtually nothing is known regarding the in vivo blocking activity of these compounds in acute inflammatory reactions.

There remains a need for new methods which block events leading to inflammatory lung injury and the diseases which result in inflammatory lung injury.

SUMMARY OF THE INVENTION

Accordingly, one object of this invention is to provide a novel method for treatment and prevention of selectin-dependent acute lung injury and diseases which result from selectin-dependent acute lung injury.

It is another object of the present invention to provide a method for treatment and prevention of selectin-dependent acute lung injury and diseases which has reduced tendency to cause side effects than conventional methods.

It is another object of the present invention to provide pharmaceutical compositions for the treatment and prevention of inflammatory lung injury and diseases which are selectin-dependent.

These and other objects, which will become apparent during the following detailed description, have been achieved by the inventor's discovery that selectin-dependent acute lung injury and diseases which result therefrom may be prevented by the administration of an effective amount of a sulfatide.

DESCRIPTION OF THE PREFERRED EMBODIMENTS

The present inventors have now discovered that sulfatide, which is a known ligand for L-selectin, facilitates in vitro binding of rat neutrophils in a manner that is position-dependent for the sulfate group on the galactose molecule. Using the two models of acute lung injury, treatment of animals with sulfatide has been found to be strongly protective against development of lung injury, as defined by reduced permeability and hemorrhage. These protective effects are related to diminished neutrophil accumulation in lung tissues, as defined by myeloperoxidase (MPO).

Sulfatides useful in accordance with the present invention include native sulfatides which can be obtained commercially (such as bovine brain sulfatide available from Sigma, St. Louis, Mo.), can be isolated from brain tissue or can be synthetically produced, as described by Suzuki et al. (*Biochem. Biophys. Res. Commun.* 190, 426 (1993); incorporated herein by reference). Preferably bovine brain sulfatide is used.

Alternatively, sulfatide gangliosides can also be used in accordance with the present invention. These can be isolated as described by Handa et al. (*Biochem. Biophys. Res. Commun.* 175, 1 (1991)).

Alternatively, sulfatide analogs can be used. Suitable sulfatide analogs are of the formula (I)

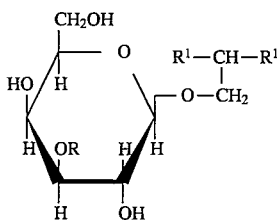

where

R is $SO_3$; and $R^1$ is —$(CH_2)_n$–$CH_3$ where n is an integer from 10 to 30, preferably 20–30, particularly preferably 30. These sulfatide analogs can be synthesized as described by Suzuki et al., (Biochem. *Biophys. Res. Commun.* 190, 426 (1993)

The selectin-dependent acute lung injury and diseases which can be treated in accordance with the present invention may include adult respiratory distress syndrome, chronic obstructive pulmonary disease and other lung inflammatory conditions.

The present method may be carried out by administering an effective amount of a sulfatide in any convenient manner such as intravenous administration or administration to the airway of a patient.

When the sulfatide is delivered intravenously, the sulfatide is first combined with a pharmaceutically acceptable carrier. Preferably buffered sterile saline is used as the carrier.

When the sulfatide is delivered via the patient's airway, the sulfatide in preferably in the form of a pharmaceutically acceptable aerosol spray. As defined herein, aerosol spray includes any composition of matter in which particles or droplets are suspended or dispersed in a gaseous medium such as air. Apparatus and methods for forming aerosols are disclosed in Kirk-Othmer, Encyclopedia of Chemical Technology, 4h Ed., vol. 1, Wiley: New York, 670–685 (1991) and Kirk-Othmer, Encyclopedia of Chemical Technology, 3rd. Ed., vol. 21, Wiley: New York, 466–483 (1983); both incorporated herein by reference. Suitable delivery systems for these aerosol sprays include conventional nasal aerosol spray bottles or aerosol delivery via conventional respiratory mechanical ventilation support equipment.

The dosage of sulfatide to be administered will, of course, be dependent on the size of the patient, the particular inflammatory disease being treated as well as the severity of the disease. In general, good results may be achieved by administering 1.0 to 3.0 mg per kg of the patient's body weight, preferably 1.0 to 3.0 mg/kg, 1 to 5 times per day, preferably 2 to 4 times per day. The exact dosage and frequency of administration will depend on clinical responsiveness and other clinical parameters.

The positive effects of the treatment of the present invention can be monitored by measuring the diminished accumulation of neutrophils in lung tissue, by monitoring the increase in permeability of the lung tissue and by measuring the decrease in hemorrhaging. As defined herein, "treatment" contemplates a decrease in the accumulation of neutrophils in lung tissue by 25 to 75%, and similar reductions in permeability of the lung tissue and in hemorrhage.

Preferably, treatment is begun at the onset of lung inflammation or at the time the disorder is first diagnosed. However, good results may be obtained even if the lung inflammatory disease has progressed. The treatment is preferably continued until the patient experiences relief from the inflammation, particularly preferably until 5 days thereafter to prevent recurrence. However, even treatment which is halted before the patient is completely free of lung inflammation is beneficial.

The process of the present invention can involve administering sulfatides as the sole active ingredient or coadministering sulfatides and other currently employed anti-inflammatory drugs such as corticosteroids, aminophyllines, interleukins (particularly IL-4 and IL-10), etc.

In another embodiment, the present invention provides pharmaceutical compositions for the treatment and prevention of selectin-dependent lung inflammatory injury, which comprise, as the active ingredient, sulfatides. Pharmaceutical compositions for the treatment and prevention of selectin-dependent lung inflammatory injury, which comprise sulfatides and at least one other anti-inflammatory drug such as corticosteroids, aminophyllines, interleukins (particularly IL-4 and IL-10), etc., are also within the scope of the present invention.

The present invention can be used to treat lung inflammation in any mammal, including rats, mice, rabbits, dogs, cows, horses, sheep, monkeys, cats, pigs and humans. Preferably, the present method is used to treat humans.

Having generally described this invention, a further understanding can be obtained by reference to certain specific examples which are provided herein for purposes of illustration only and are not intended to be limiting unless otherwise specified.

EXAMPLES

In vitro binding of sulfatides to neutrophils

In the first series the extent to which neutrophils obtained from rat blood would exhibit in vitro binding to sulfatides (Y. Suzuki, et al., *Biochem. Biophys. Res. Comm.* 190, 426 (1993)) which were present on plastic surfaces of 96 well microliter plates was determined.

In two separate experiments (Table 1, Exps. A & B), six- to 10-fold increased binding of neutrophils to bovine brain sulfatide ($I^3SO_3$GalCer) was demonstrated, with the binding being only partly blocked by the presence of the chelator for divalent cations, 5 mM EDTA. In Exp. B, neutrophil binding to sulfatide was 10-fold greater than that found with uncoated plastic wells. Deletion of sulfate in position 3 (GalCer) totally abolished neutrophil binding. When a long chain saturated alcohol containing 30 carbons (B30) was substituted for Cer, substantial binding of neutrophils (nearly 6-fold increase over controls) was also found.

The position of the sulfate on the Gal molecule was critical for neutrophil binding, with position 3 being the most facilitative of binding (Table 1, Exp. B). A similar pattern for binding of soluble recombinant rat L-selectin to sulfatide analogues has been recently described (Y. Suzuki, et al., *Biochem. Biophys. Res. Comm.* 190, 426 (1993)).

TABLE 1

| Binding of Rat Neutrophils to Sulfatide and Related Compounds* | | |
|---|---|---|
| Exp. | Surfaces | Number of Cells Bound |
| A | None | 9,012 ± 2,703 |
|  | Sulfatide ($I^3SO_3$ GalCer) | 54,358 ± 2,591 |
|  | Sulfatide + 5 nM EDTA | 30,361 ± 4,168 |
| B | None | 3,735 ± 469 |
|  | $I^3SO_3$ GalCer | 38,960 ± 4,224 |
|  | GalCer | 3,250 ± 1,173 |
|  | $I^3SO_3$ GalB30 | 20,418 ± 3,051 |
|  | $I^4SO_3$ GalB30 | 4,224 ± 1,173 |
|  | $I^2SO_3$ GalB30 | 781 ± 49 |
|  | $I^6SO_3$ GalB30 | 305 ± 70 |

*Methodological details are provided in Suzuki et al., Biochem. Biophys. Res. Comm. 190, 426 (1993).

Effects of sulfatide in in vivo models of inflammatory lung injury

A. Acute lung injury induced by intravenous infusion of purified cobra venom factor Bovine brain sulfatide in rats were employed in the two in vivo models of inflammatory lung injury which have been shown to be neutrophil and selectin-dependent. In the first model, acute lung injury is induced by intravenous infusion of purified cobra venom factor (CVF), resulting in acute lung injury that is L- and P-selectin-dependent (M. S. Mulligan et al, *J. Immunol.*, In press (1994); M. S. Mulligan et al., *J. Clin. Invest.* 90, 1600 (1992)). Sulfatide was sonicated in sterile saline containing 1 mg/ml bovine serum albumin, resulting in formation of microdroplets. 0.25–1.0 mg sulfatide was infused intravenously (in a volume of 0.3 ml) immediately prior to intravenous infusion of CVF together with $^{125}$I-albumin and $^{51}$Cr-rat RBC, as described in detail elsewhere (M. S. Mulligan et al., *J. Clin. Invest.* 90, 16001(1992)). Animals were sacrificed 30 min later. Lung radioactivity was measured and compared to the amount of radioactivity present in 1.0 ml blood obtained from the inferior vena cava at the time of sacrifice. This permitted calculation of permeability and hemorrhage indices, reflective of the extent of lung injury (a measure of leakage of albumin and RBC into the lung). This, in turn, allowed us to calculate the protective effects of the interventional agents (M. S. Mulligan et al., *J. Clin. Invest.* 90, 1600 (1992)). In addition, neutrophil accumulation in lung, as reflected by tissue content of myeloperoxidase (MPO), was also measured by the decomposition of $H_2O_2$ in the presence of O-dianisidine (M. S. Mulligan et al., *J. Clin. Invest.* 90, 1600 (1992)). The results are summarized in Table 2, Exp. A. Treatment of rats with brain sulfatide (given intravenously just before the infusion of CVF) produced dramatic reductions in permeability, hemorrhage and MPO content. These were infused intravenously with 1.0 mg bovine brain sulfatide and blood neutrophil counts performed at 5 min intervals until 30 min later, the change in blood neutrophil counts as compared to the value prior to sulfatide infusion never varied by more than 10% (data not shown). Thus, the protective effects of sulfatide cannot be explained by induction of neutropenia.

B. Acute lung inflammatory injury induced by intrapulmonary deposition of IgG immune complexes The second model of acute lung inflammatory injury involved intrapulmonary deposition of IgG immune complexes, leading to extensive intraalveolar recruitment of neutrophils and injury that peaks at 4 hr (K. J. Johnson and P. A. Ward, *J. Clin Invest.* 54, 349 (1974)). The injury is initiated by the intratracheal instillation of rabbit polyclonal TgG antibody to bovine serum albumin (BSA) and the intravenous injection of BSA. As with the model described above. $^{125}$I-albumin and $^{51}$Cr-rat RBC are infused intravenously at time O and injury was similarly quantitated (at 4 hr). In this model, the recruitment of neutrophils is L- and E-selectin-dependent (M. S. Mulligan et al, *J. Immunol.*, In press (1994); M. S. Mulligan et al., *J. Clin. Invest.* 88, 1396 (1991)). Rats undergoing lung inflammatory injury induced by immune complexes were treated at 2.5, 3.0 and 3.5 hr with intravenous infusions of brain sulfatide (1.0 mg at each interval). These infusion schedules were timed to coincide with the period of rapid neutrophil accumulation in lung (M. S. Mulligan et al., *J. Clin. Invest.* 88, 1396 (1991); J. S. Warren et al., *Free Rad. Biol. Med.* 8, 163 (1990)). The results are shown in Table 2, Exp. B.

TABLE 2

Protective Effects of Sulfatides and Sulfated Glycolipid in Acute Lung Injury

| Models of Lung Injury | Material Infused Intravenously | Amount (mg) | Reduced (%) Permeability | Hemorrhage | MPO |
|---|---|---|---|---|---|
| A. Systemic activation of complement* | brain sulfatide | 1.0 | 80 (<.001) | 64 (<.001) | 66 (<.001) |
| | brain sulfatide | 0.5 | 38 (.001) | 36 (.012) | 34 (.004) |
| | brain sulfatide | 0.1 | 2 (N.S.) | 6 (N.S.) | 4 (N.S.) |
| | brain sulfatide, desulfated | 1.0 | <2 (N.S.) | <2 (N.S.) | 4 (N.S.) |
| | sulfated brain ganglioside | 1.0 | 45 (.001) | 43 (.014) | 40 (.002) |
| | sulfated brain ganglioside | 0.5 | 25 (.021) | 21 (N.S.) | 20 (.042) |
| | desulfated brain ganglioside | 1.0 | <2 (N.S.) | <2 (N.S.) | <2 (N.S.) |
| B. IgG immune complex** | brain sulfatide | 1.0 | 53 (<.001) | 55 (<.001) | 49 (N.001) |
| | brain sulfatide, desulfated | 1.0 | <2 (N.S.) | <2 (N.S.) | <2 (N.S.) |

*Compounds were infused intravenously at time 0, just before CVF. The negative and positive control values for permeability, hemorrhage and MPO are: 0.10 ± .005 and 0.53 ± .01; 0.02 ± .001 and 0.15 ± .004; and 0.11 and 0.11 ± .02 and 0.51 ± .02, respectively. For each data group, n = 5. Values present mean reductions in permeability, hemorrhage and MPO. The numbers in parenthesis represent p-values (derived by analysis of variance), using comparisons to positive controls that were not treated with any of the listed compounds.
**Compounds were infused intravenously in the amounts indicated at 2.5, 30 and 3.5 hr after initiation of immune complex deposition. The negative and positive controls for permeability, hemorrhage and MPO were: o.16 ± .01 and 0.61 ± .02; 0.04 ± .001 and 0.25 ± .02; and 0.11 ± .02 and 0.68 ± .02, respectively. For each data group, n = 5. The numbers in parenthesis represent p-values (derived from analysis of variance) when compared to positive controls that were not treated with any of the listed compounds.

effects were dose-dependent (Table 2). The desulfated sulfatide exhibited no protective effects. In addition, sulfated brain ganglioside (A. Handa et al., *Biochem. Biophys. Res. Comm.* 175, 1 (1991)) demonstrated protective activity whereas its desulfated preparation did not. These data suggest that, in this model of inflammatory lung injury, sulfatide and sulfated ganglioside are significantly protective in a manner that is correlated with reduced neutrophil recruitment. The protective effects of sulfatide were not related to an effect on blood neutrophil counts. When rats (n=4 each)

As is apparent from the data, sulfatide had significantly protective effects on permeability and hemorrhage changes and, in parallel, caused reduction in lung MPO content. In contrast, the desulfated form of sulfatide was without effect either on the parameters of injury or on lung content of MPO.

Precisely what selectin(s) is/are being blocked by sulfatide is not clear at present. Sulfatides have been shown to be reactive with rat L-selectin (Y. Suzuki, et al., *Biochem.*

*Biophys. Res. Comm.* 190, 426 (1993)), and this is supported by the data in Table 1 where binding of intact rat neutrophils to solid phase sulfatide is demonstrated. It is also possible that infused sulfatide was reactive with either P-selectin (in the case of the CVF model of lung injury) or E-selectin (in the case of IgG immune complex-induced lung injury). Sulfoglucuronyl glycosphingolipids have been reported to bind to P- and L-selectins but not to E-selectin (L. K. Needham et al., *Proc. Natl. Acad. Sci. USA* 90, 1359 (1993)). The bulk of evidence related to interactions of sulfated compounds with selectins suggests that E-selectin is less reactive when compared to P- and L-selectin (G. Todderud et al., *J. Leukoc. Biol.* 52, 85 (1992)).

The above data demonstrate that sulfatide has substantial protective effects in two models of selectin-dependent acute inflammatory lung injury in rats. The protective effects appear to be correlated with reduced recruitment of neutrophils into lung tissue. The extent of protective activity of sulfatide is at least as good as, if not better than that found with these other protective agents. In addition, sulfatides are naturally recurring compounds that can be obtained either by extraction from bovine brain or chemically synthesized. The substantial degree of protection from neutrophil-induced lung injury provided by the use of sulfatide suggests a novel approach to the blocking of select-independent inflammatory responses.

Having now fully described the invention, it will be apparent to one of ordinary skill in the art that many changes and modifications can be made thereto without departing from the spirit or scope of the invention as set forth herein.

What is claimed as new and is desired to be secured by Letters Patent of the United States is:

1. A method of treating selectin-dependent lung inflammation in a patient in need thereof comprising,
administrating an effective amount of a sulfatide.

2. The method of claim 1, wherein said sulfatide is a brain sulfatide.

3. The method of claim 2, wherein said sulfatide is bovine brain sulfatide.

4. The method of claim 1, wherein said sulfatide is of the formula (I):

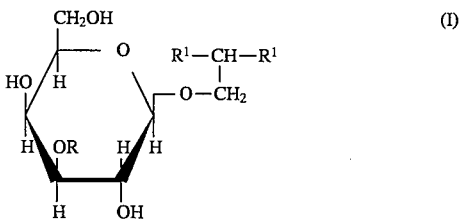

where

R is $SO_3$; and $R^1$ is $—(CH_2)_n—CH_3$ where n is an integer of from 10 to 30.

5. The method of claim 4, wherein n is of from 20 to 30.

6. The method of claim 5, wherein n is 30.

7. The method of claim 1, wherein said sulfatide is a sulfatide ganglioside.

8. The method of claim 1, wherein said effective amount is 1.0 to 3.0 mg/kg based on the body weight of the patient.

9. The method of claim 1, wherein said administration is performed 1 to 5 times per day.

10. The method of claim 1, wherein said sulfatide is administered to the airway of said patient.

11. The method of claim 10, wherein said sulfatide is administered in the form of a pharmaceutically acceptable aerosol spray.

12. The method of claim 1, wherein said sulfatide is administered intravenously.

* * * * *